United States Patent [19]

Roberts-Lewis et al.

[11] Patent Number: 5,430,039
[45] Date of Patent: Jul. 4, 1995

[54] TREATMENT OF NEUROLOGICAL DISORDERS

[75] Inventors: Jill M. Roberts-Lewis; Michael E. Lewis, both of Landenberg, Pa.

[73] Assignee: Cephalon, Inc., West Chester, Pa.

[21] Appl. No.: 208,050

[22] Filed: Mar. 8, 1994

Related U.S. Application Data

[63] Continuation of Ser. No. 838,598, Feb. 19, 1992, abandoned, which is a continuation of Ser. No. 590,112, Sep. 28, 1990, abandoned.

[51] Int. Cl.$^6$ .............................................. A61K 31/44
[52] U.S. Cl. .................................... 514/297; 514/313
[58] Field of Search ............................ 514/297, 313

[56] References Cited

U.S. PATENT DOCUMENTS 3,830,918  8/1974  Molnar et al. ...................... 424/257
4,840,972  6/1989  Effland et al. ...................... 514/313

OTHER PUBLICATIONS

Rosner et al., Thérapie, XXII:345–354, 1967, "Influence de La chloroquine et de L'hydroxychloroquine sur L'evolution des troubles moteurs post-ischémiques," with attached translation.
Rosner et al., "Thérapie, XXII:355–360, 1967, Hydroxychloroquine et résistance corticale è L'anoxie asphyxique," with attached translation.
Larsen et al., Thérapie, 33:651–660, 1978, "Modèle d'ischémie cérébrale expérimentale par microsphères chez le Rat Etude de l'effet de deux extraits de Ginkgo biloba et du naftidrofuryl," with attached translation.
Faden et al., Science, 244:798–800 (1989).
Choi et al., Annual Rev. Of Neuros., 13:171–182 (1990).
Hostetler and Jellison, Mol. Cell. Biochem., 88:77–82 (1989).
Lazarewicz et al., Neuropharmacol., 27:765–769 (1988).
Otamiri and Tagesson, Am. J. Surg., 157:562–565 (1989).
Otani et al., Am. J. Physiol., 257:H252–H258 (1989).
Giulian and Robertson, Ann. Neurol., 27:33–42 (1990).
Murphy et al., FASEB J, 4:1624–1633 (1990).
Badalamente et al., J. of Hand Surgery, 11:337–340 (1986).
Iizuka et al., J. of Neurosurgery, 65:92–98 (1986).
Giulian et al., J. of Neurosci, 9:4416–4429 (1989).
Siman et al., J. of Neurosci., 9:1579–1590 (1989).
Matsuzawa et al., J. Biol. Chem., 255:5190–5194 (1980).
Siesjo (1981), J. Cereb. Blood Flow Metabol., 1:155–185 (1981).
Yawo and Kuno, Science, 222:1351–1353 (1983).
Au et al., J. Cell Biochem, 27:449–453 (1985).
Barbour et al., Nature, 342:918–920 (1989).
DeGeorge et al., J. Neurosci. Res., 21:323–332 (1988).
Reuter, Nature, 301:569–574 (1983).
Goldschmidt et al., Proc. Natl. Acad. Sci. 77:3047–3051, (1980).
Chien et al., The J. of Biol. Chem. 253:4809–4817, (1978).
Norris et al. 1986, British Medical J, vol. 292 pp. 21–23.
Jastremski et al. 1989, JAMA, vol. 262(24) pp. 3427–3430.
Jun et al. CA 68:113285u 1968.
Rosner et al. CA 66:114464x 1967.
Larsen et al. CA 90:115360t 1979.

Primary Examiner—Marianne M. Cintins
Assistant Examiner—Russell Travers
Attorney, Agent, or Firm—Fish & Richardson; Richard P. Burgoon, Jr.

[57] ABSTRACT

A method for inhibiting neuronal cell death in a mammal resulting from a disorder of the central or peripheral nervous system including administering to the mammal a neuronal cell death inhibitng amount of a preparation including any of mepacrine, chloroquine, or hydroxychloroquine, the preparation being essentially free of colchicine.

16 Claims, 3 Drawing Sheets

# TREATMENT OF NEUROLOGICAL DISORDERS

This application is a continuation of application Ser. No. 07/838,598, filed Feb. 19, 1992, which is a continuation of application Ser. No. 07/590,112, filed Sep. 28, 1990, both of which have been abandoned.

BACKGROUND OF THE INVENTION

The invention relates to the use of non-peptide compounds to prevent cell death characteristic of neurological disease or injury.

Calcium-dependent mechanisms have been proposed to mediate the cell death that occurs in many neurological disorders, including: Alzheimer's disease, which is characterized by degeneration of cholinergic cells in the ventral forebrain as well as of cortical and hippocampal cells; Parkinson's disease, which is characterized by degeneration of dopaminergic cells in the substantia nigra; Huntington's disease, which is characterized by a degeneration of the GABAergic (gamma amino butyric acid) cells in the basal ganglia; AIDS dementia, which involves a degeneration principally of subcortical neurons; stroke and related ischemic disorders; epilepsy; motor neuron diseases; peripheral nerve degeneration; and head and spinal cord injuries (Schanne et al., 1979, *Science*, 206:699; Siesjo, 1981, *J. Cereb. Blood Flow Metab.*, 1:155; Schwarcz et al., 1984, *Life Sci.*, 35:19; Simon et al., 1984, *J. Cereb. Blood, Flow. Metab.*, 4:350; Ben-Ari, 1985, *Neurosci.*, 14:375; Beal et al., *Nature*, 330:649; Badalamente et al., 1986, *J. Hand Surg.*, 11-B:337; Garthwaite et al., 1986, *Neurosci.*, 18:437–447; Choi, 1987, *J. Neurosci.*, 7:380; Maragos et al., 1987, *Trends. Neurosci.*, 10:65; Olney, 1987, In: *Excitatory Amino Acid Transmission*, T. P. Hicks, et al., Eds., Liss, pp.217; Meyer, 1989, *Brain Res. Rev.*, 14:227; Herrling, 1989, In: *The NMDA Receptor*, J. C. Watkins, et al., Eds., Oxford, pp. 177; Girault et al., 1990, *Trends Neurosci.*, 13:325; Dreyer et al., 1990, *Science*, 248:364).

There is converging evidence that a calcium-dependent protease activity (CAPA) may be responsible for the cellular destruction that occurs in these neuropathological states (Leonard and Salpeter, 1982, *Exp. Neurol.*, 76L121; Smith and Amaducci, 1982, *Neurochem. Res.*, 7:541; Iizuka et al., 1986, *J. Neurosurg.*, 65:92; Siman et al., 1989, *J. Neurosci.*, 9:1579). The protease Calpain I has been causally linked to neuromuscular neuropathy (Leonard et al., 1982, *Exp. Neurol.*, 76:121), as well as to neuronal death induced by excitatory amino acids (EAA) (Siman et al., 1989, *J. Neurosci.*, 9:1579).

Endogenous EAA include glutamate and aspartate, which normally appear to function as neurotransmitters, but are thought to be damaging when released excessively within the nervous system. Excessive release or infusion of EAA leads to calcium-related neuronal death, and may be an etiological agent in a number of degenerative neuropathologies, including Alzheimer's disease, Parkinson's disease, Huntington's disease, stroke, epilepsy, motor neuron diseases, and head injuries (Schanne et al., 1979, *Science*, 206:699; Schwarcz et al., 1984, *Life Sci.*, 35:19–32; Ben-Ari, 1985, *Neurosci.*, 14:375; Beal et al., 1986, *Nature*, 330:649; Badalamente et al., 1986, *J. Hand Surg.*,. 11-B:337; Garthwaite et al., 1986, *Neurosci.*, 18:437; Choi, 1987, *J. Neurosci.*, 7:380; Maragos et al., 1987, *Trends, Neurosci.*, 10:65; Olney, 1987, In: *Excitatpry Amino Acid Transmission*, T. P. Hicks, D. Lodge, and H. McLennan, Eds., Liss, pp. 217; Faden et al., 1989, *Science*, 244:798; Herrling, 1989, In: *The NMDA Receptor*, J. C. Watkins et al., Eds., Oxford, pp. 177; Choi et al., 1990., *Ann. Rev. Neurosci.*, 13:171; Girault et al., 1990, Trends Neurosci., 13:325).

Endogenous EAA toxicity may be a fundamental mechanism of cell death, mediating the ultimate neuronal destruction wrought by a multitude of injuries or diseases of the central nervous system. Because of the convergence of evidence suggesting that CAPA may be a fundamental, obligatory event underlying neuronal death in a variety of neuropathological conditions, treatments that reduce CAPA or the events leading to CAPA (such as excitatory amino acid receptor activation) could prove to have widespread use as neurotherapeutics for a diverse range of neurological disorders. For example, the non-competitive excitatory amino acid receptor antagonist, MK-801, has been shown to block both EAA- and ischemia-induced neuronal damage in vivo (Foster et al., 1987, *Neurosci. Let.* 76:307, Gill et al., 1987, *J. Neurosci.* 7:3341).

SUMMARY OF THE INVENTION

In general, the invention features a method for inhibiting neuronal cell death in a mammal, preferably a human, resulting from a disorder, e.g., a disease or an injury, preferably from a calcium-related disorder of the central or peripheral nervous system, e.g., Alzheimer's disease, Parkinson's disease, Huntington's disease, AIDS dementia, stroke and related ischemic/anoxic events, epilepsy, motor neuron diseases, peripheral nerve degeneration, or head or spinal cord injuries, including administering to the mammal a neuronal cell death inhibiting amount of a preparation comprising any of mepacrine, chloroquine, or hydroxychloroquine, the preparation being essentially free of colchicine.

In preferred embodiments the method includes administering to the mammal a neuronal cell death inhibiting amount of a compound which blocks excitatory amino acid receptors, or which blocks other receptors which mediate calcium entry, e.g., receptor antagonists for angiotensin II or bradykinin, and/or calcium channel antagonists, e.g., flunarizine, verapamil, nimodipine, or nifedipine.

In preferred embodiments, the methods of the invention are useful for preventing cell death occurring in the hippocampus, at cholinergic neurons, in the substantia nigra, in the ventral forebrain, at a neuron that bears a nerve growth factor receptor, in the nucleus basalis of Meynert, at a GABAergic neuron, i.e., a neuron which uses gamma amino butyric acid as a transmitter substance, at dopaminergic neurons, in the basal ganglia, at cortical neurons, in the septum, or at a cell that has been subjected to ischemia, hypoxia, anoxia, or hypoglycemia.

In other preferred embodiments, the treatment of the invention is administered after the onset of the disorder, preferably within one hour after the onset of the disorder.

The treatments of the invention can also be used to inhibit cell death in non-neural tissue, e.g., muscle tissue, e.g., smooth muscle, e.g., cardiac muscle.

A calcium related disorder, as used herein, is a neurological disorder, e.g., a disease or an injury, that is thought to involve calcium sensitive neuronal degeneration, e.g., the neuronal degeneration that results from an alteration in the flow of calcium within or across the cell membrane of a neuronal cell.

Mepacrine (also known as Quinacrine, Merck Monograph number 8053, *The Merck Index*, 11th Ed., Merck, Rahway N.J., hereby incorporated by reference) was originally developed as a potential antimalarial drug by Mietzsch and Mauss, and is described in Ger. Pats. 553,072 and 571,499 and U.S. Pat. No. 2,113,357. Chloroquine (Merck Monograph number 2163, *The Merck Index*, 11th Ed., supra) has largely replaced mepacrine for the treatment of malaria due to its lower toxicity. Chloroquine is described in Ger. Pat. 683,692 and U.S. Pat. No. 2,233,970. Hydroxychloroquine (also known as oxychloroquine and oxichlorochine, Merck Monograph number 4748, *The Merck Index*, 11th Ed., supra), in which one of the N-ethyl substituents of chloroquine is beta-hydroxylated, has been used in the treatment of rheumatoid arthritis and malaria. The uses and pharmacology of mepacrine, chloroquine and hydroxychloroquine have been reviewed in The Pharmacological Basis of Therapeutics, (*The Pharmacological Basis of Therapeutics*, 5th ed., L. S. Goodman et al., Eds., Macmillan, 1975, pp. 1030-1031; 1049-1053; ibid., 7th ed., L. S. Goodman et al., Eds., Macmillan, 1985, pp. 1032-1035; 1054-1055, hereby incorporated by reference; and in Martindale, The Extra Pharmacopoeia, (29th ed., J. E. F. Reynolds, Ed., pp. 508-514, The Pharmaceutical Press, 1989).

Other features and advantages of the invention will be apparent from the following description of the preferred embodiments, and from the claims.

DESCRIPTION OF THE PREFERRED EMBODIMENTS

The drawings are first described.

Figure 1:
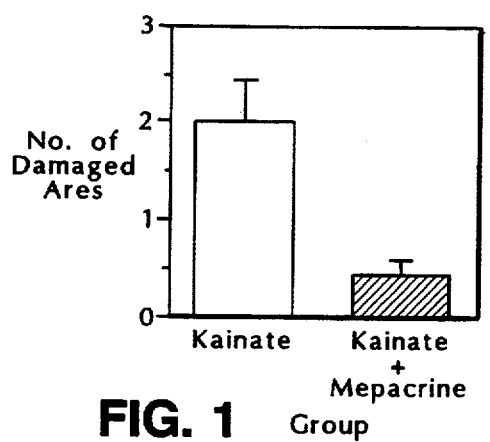
FIG. 1 is a graph of the effect of mepacrine on kainate-induced neuronal degeneration in the hippocampus.
Figure 2:
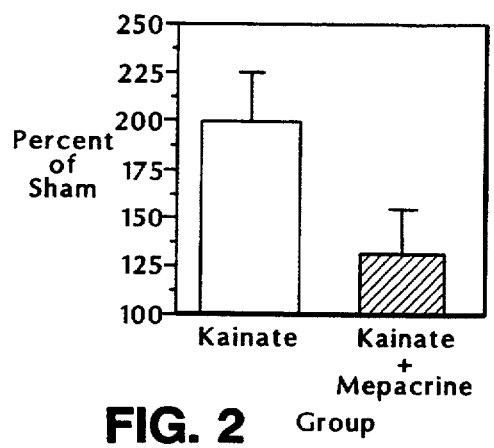
FIG. 2 is a graph of the effect of mepacrine on kainate-induced spectrin breakdown in the hippocampus.

Treatment with mepacrine, chloroquine or hydroxychloroquine reduces EAA-induced neuronal damage Intracerebroventricular (icy) treatment with mepacrine significantly reduced both kainate-induced hippocampal damage and kainate-induced spectrin proteolysis in the dorsal hippocampus. Because EAA-induced spectrin proteolysis precedes and appears to be causally related to the subsequent neuronal death produced by EAA (Siman et al., 1989, *J. Neurosci.*, 9:1579), measurement of the proteolytic event can be used to provide an index of neuronal injury and thus of the efficacy of a compound in reducing neuronal injury and subsequent cell death. FIG. 1 shows the effect of mepacrine on kainate-induced neuronal degeneration in the hippocampus. In FIG. 1 cannulated rats received 160 nmol of mepacrine (cross hatched bar), or vehicle (solid bar), by icv infusion, 10 minutes prior to and 3 hours following icv infusion of kainic acid. The rats were killed two weeks later, and damage to the hippocampus was evaluated as described below. Data shown are the mean number of CA-regions of the hippocampus damaged for each group, $\pm$S.E.M. Mepacrine decreased the number of damaged areas within the hippocampus from approximately $2\pm0.4$ (in the absence of mepacrine) to approximately $0.4\pm0.2$ (in the presence of mepacrine). FIG. 2 shows the effect of mepacrine on kainate-induced spectrin breakdown in the hippocampus. In FIG. 2 cannulated rats received 160 nmol of mepacrine (crosshatched bar), or vehicle (solid bar), by icv infusion, immediately prior to icy infusion of kainic acid. Cannulated sham control animals received two infusions of vehicle, but no kainate or mepacrine. All rats were killed 24 hours later, and homogenates of the dorsal hippocampus were analyzed for spectrin breakdown as described below. The magnitude of spectrin proteolysis is expressed as a percent increase in spectrin breakdown products over sham control values. Data shown are the mean percent increase in spectrin breakdown products for each group (sham=100%)$\pm$S.E.M. Icv infusion of kainate led to an increase of approximately $95\pm25\%$ above sham value in the amount of spectrin breakdown products in the dorsal hippocampus. When mepacrine was administered by icy infusion immediately prior to kainate infusion an increase of only approximately $25\pm25\%$ above the sham value in the amount of spectrin breakdown products was seen.

Figure 3:
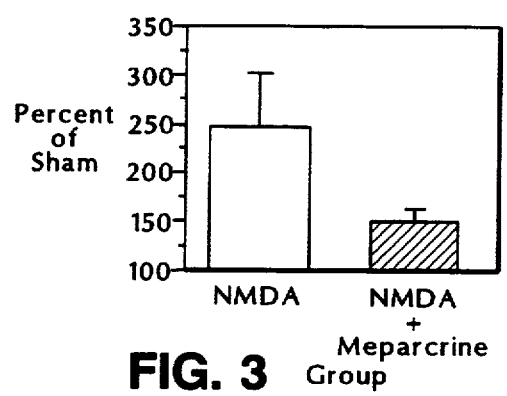
FIG. 3 is a graph of the effect of mepacrine on NMDA-induced spectrin breakdown in the hippocampus.

As shown in FIG. 3, mepacrine was also effective in reducing N-methyl-D-aspartate (NMDA)-induced spectrin breakdown in the dorsal hippocampus. In FIG. 3 rats received 40 mg/kg of mepacrine (crosshatched bar), or vehicle (solid bar), intraperitoneally (ip), immediately following icv infusion of NMDA. Sham control animals received an icv infusion of vehicle, but no NMDA or mepacrine. All rats were killed 24 hours later, and homogenates of the dorsal hippocampus were analyzed for spectrin breakdown, as described below. The magnitude of spectrin proteolysis is expressed as a percent increase in spectrin breakdown products over sham control values. Data shown are the mean percent increase in spectrin breakdown products for each group (sham=100%)$\pm$S.E.M. Infusion of NMDA led to a an increase of approximately $140\pm50\%$ above the sham value in the amount of spectrin breakdown products. When mepacrine was administered intraperitoneally immediately following icv infusion of NMDA, there was an increase of only approximately $50\pm10\%$ above sham value in spectrin breakdown products.

Figure 4:
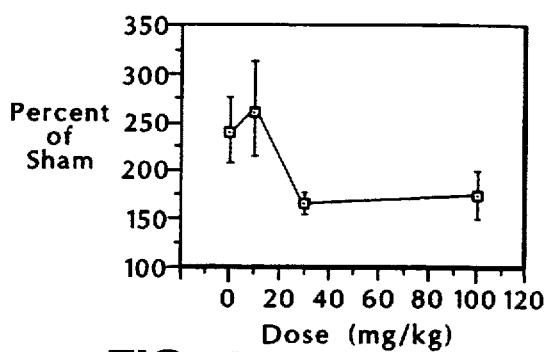
FIG. 4 is a graph of the effect of systemic mepacrine treatment on NMDA-induced spectrin breakdown.

A separate set of experiments examined the effect of various mepacrine dosages on NMDA-induced spectrin proteolysis in the dorsal hippocampus. As shown in FIG. 4, intraperitoneal injection of either 30 mg/kg or 100 mg/kg of mepacrine substantially reduced NMDA-induced spectrin breakdown. In FIG. 4 the x-axis indicates the mepacrine dosage in mg/kg. The y-axis indicates the level of spectrin breakdown products found in treated animals expressed as a percentage of the level of such products found in sham control animals. i.e., animals which were given vehicle instead of mepacrine and NMDA. As shown in FIG. 4, rats received 10, 30 or 100 mg/kg of mepacrine, or vehicle (0 mg/kg), ip, immediately following icv infusion of NMDA. Sham control animals received an icv infusion of vehicle, but no NMDA or mepacrine. All rats were killed 24 hours later, and homogenates of the dorsal hippocampus were analyzed for spectrin breakdown as described in the text. The magnitude of spectrin proteolysis is expressed as a percent increase in spectrin breakdown products over sham control values. Data shown are the mean percent increase in spectrin breakdown products at each dose (sham=100%)±S.E.M.

Figure 5:
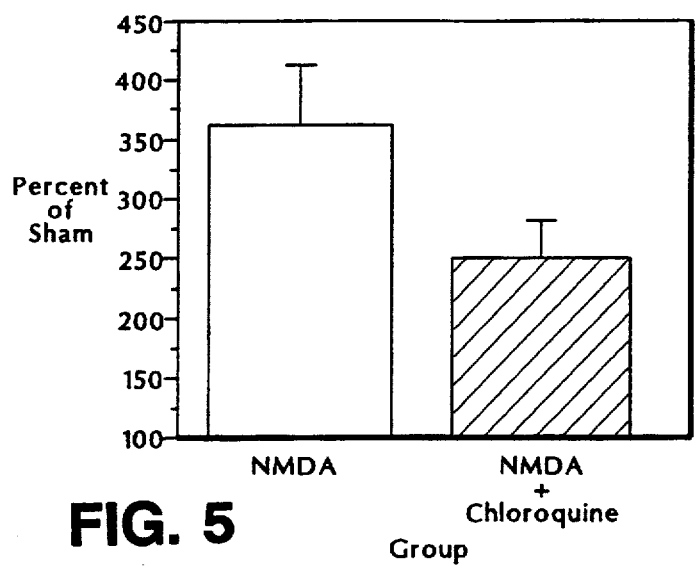
FIG. 5 is a graph of the effect of chloroquine on NMDA-induced spectrin breakdown.
Figure 6:
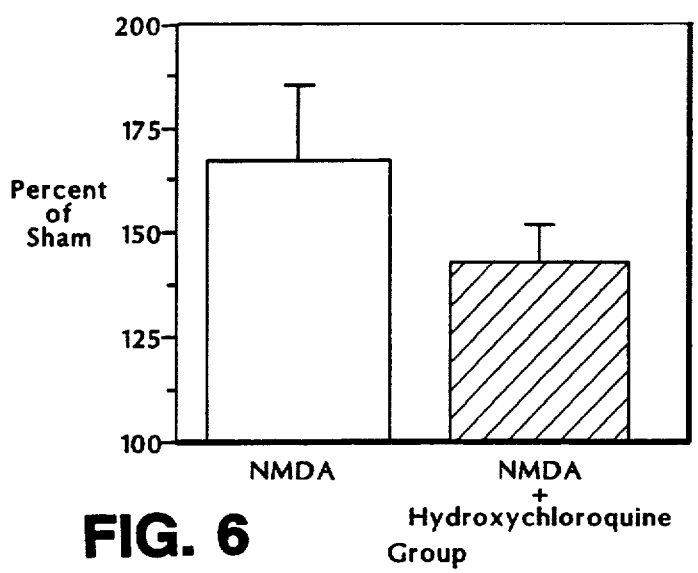
FIG. 6 is a graph of the effect of hydroxychloroquine on NMDA-induced spectrin breakdown.

Chloroquine and hydroxychloroquine, two compounds structurally related to mepacrine, were also found to reduce NMDA-induced spectrin breakdown in the dorsal hippocampus. In the study depicted in FIG. 5, infusion of NMDA led to an increase of approximately 260±40% above the sham value in the amount of spectrin breakdown products, while simultaneous icv infusion of chloroquine and NMDA led to an increase of only approximately 140±30% above sham value. As shown in FIG. 5, rats received NMDA and 100 nmol of chloroquine (crosshatched bar), or vehicle (solid bar), icv. Sham control animals received an icv infusion of vehicle, but no NMDA or chloroquine. All rats were killed 24 hours later, and homogenates of the dorsal hippocampus were analyzed for spectrin breakdown as described below. The magnitude of spectrin proteolysis is expressed as a percent increase in spectrin breakdown products over sham control values. Data shown are the mean percent increase in spectrin breakdown products for each group (sham=100%)±S.E.M. In the study depicted in FIG. 6, infusion of NMDA led to an increase of approximately 65±20% above sham value in the amount of spectrin breakdown products; when hydroxychloroquine was administered icv at the same time as the NMDA infusion there was an increase of only approximately 30±10% above sham value in the amount of spectrin breakdown products. As shown in FIG. 6, rats received NMDA and 200 nmol of hydroxychloroquine (cross hatched bar), or vehicle, (solid bar), by icv infusion. Sham control animals received an icv infusion of vehicle, but no NMDA or hydroxychloroquine. All rats were killed 24 hours later, and homogenates of the dorsal hippocampus were analyzed for spectrin breakdown as described below. The magnitude of spectrin proteolysis is expressed as a percent increase in spectrin breakdown products over sham control values. Data shown are the mean percent increase in spectrin breakdown products for each group (sham=100%)±S.E.M.

Kainate infusion regime

The effect of mepacrine on kainate-induced neuronal damage was evaluated as follows. Adult female Sprague Dawley rats (220-250 g) were anesthetized with Nembutal (50 mg/kg, intraperitoneally) and administered mepacrine (160 nmol in 5μl) or vehicle, by icv infusion 10 minutes before and 3 hours following infusion of kainate (2.5 nmol in 1 μl) into the lateral ventricles. Control animals received vehicle instead of kainate and mepacrine. Icv infusions were delivered through cannulae permanently implanted at stereotaxic coordinates: anterior-posterior at bregma, 1.5 mm lateral to bregma, and 4.4 mm ventral from the top of the skull. Results of this treatment protocol were evaluated using the anatomical analysis described below.

In studies to assess the effect of kainate on spectrin proteolysis, rats received an icv infusion of mepacrine (160 nmol in 5 μl) or vehicle immediately prior to icv infusion of kainate. Icv infusions were performed as described above. These rats were killed 24 hours later and subject to biochemical analysis as described below.

NMDA infusion regime

The effect of mepacrine, chloroquine and hydroxychloroquine on NMDA-induced hippocampal damage was evaluated as follows. Female Sprague-Dawley rats (200-250 g) were anesthetized with Nembutal (50 mg/kg, intraperitoneally) and administered NMDA (3 μg in 1 μl) into the hippocampus at stereotaxic coordinates −3.3 mm posterior from bregma, lateral 2.3 mm from the midline, and ventral 4.3 mm from the top of the skull. Mepacrine or vehicle was administered either directly into the hippocampus (20 or 160 nmol in 1 μl) simultaneously with the infusion of NMDA or peripherally (10-100 mg/kg, intraperitoneally) immediately following the intrahippocampal infusion of NMDA. 100 nmol of chloroquine or hydroxychloroquine was coadministered with 3 μg NMDA in 1 μl into the hippocampus at the sterotoxic coordinates given above. Control animals received two infusions of vehicle instead of NMDA and one of the three drugs. In all cases the rats were killed 24 hours later, and homogenates of the dorsal hippocampus were prepared for the biochemical analysis described below.

Anatomical and Biochemical Analyses

Anatomical analysis was performed as follows. Rats were killed by decapitation 2 weeks following treatment, and the brains were rapidly removed and frozen on dry ice. A series of slide-mounted coronal sections from each brain was stained with thionin and examined microscopically. Damage to the hippocampus was quantified by summing the total number of 4 anatomically defined regions of the hippocampus (CA 1-4 according to the classification of Lorente de No, as described by Shepard, 1979, *The Synaptic Organization of the Brain*, Oxford, p. 310, hereby incorporated by reference), on both left and right sides of the brain, that suffered a loss of pyramidal cells.

Biochemical analysis was performed as follows. Calpain I-sensitive proteolysis of brain spectrin (fodrin) was evaluated in homogenates of the hippocampus using an immunoblot analysis described by Siman et al. (1988, Neuron, 1:279-287, hereby incorporated by reference). Briefly, rats were killed by decapitation 24 hours following treatment, and the dorsal hippocampus was rapidly dissected out of the brain and homogenized in 20 mM Tris-HCl (pH 7.4) containing 0.1 mM phenylmethylsulfonyl-fluoride. Proteins from aliquots of each homogenate were separated by SDS-PAGE, and an immunoblot analysis was used to quantitate the amount of kainate or NMDA-induced spectrin breakdown in each sample.

Figure 7:
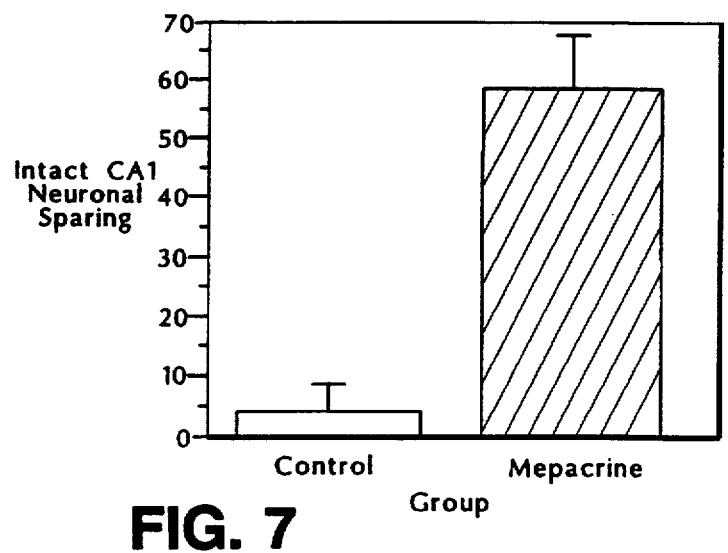
FIG. 7 is a graph of the effect of mepacrine treatment on ischemia-induced hippocampal damage.

Treatment With MepaCrine Dramatically Reduces Ischemia-Induced Hippocampal Damage When gerbils were given repeated, systemic treatments with mepacrine, there was a remarkable reduction in the extent of hippocampal damage sustained after transient cerebral ischemia. As shown in FIG. 7, gerbils treated with mepacrine had approximately 55±10% sparing of CA1 pyramidal cells, while only approximately 4±3% sparing of CA1 pyramidal cells was observed in untreated gerbils. As shown in FIG. 7, gerbils received mepacrine (80 mg/kg, ip) (cross hatched bar), or vehicle (control) (solid bar), immediately prior to, and once a day (40 mg/kg, ip) for 6 days after bilateral occlusion of the carotid arteries. The gerbils were killed on the sixth post-operative day, and damage to the CA1 region of the hippocampus was evaluated as described below. The mean size of the intact (spared) pyramidal cell layer is expressed above as a percentage of the total CA1 pyramidal cell subfield for each group, ±S.E.M.

(0%=total neuronal loss; 100%=maximum-possible sparing).

Figure 8:
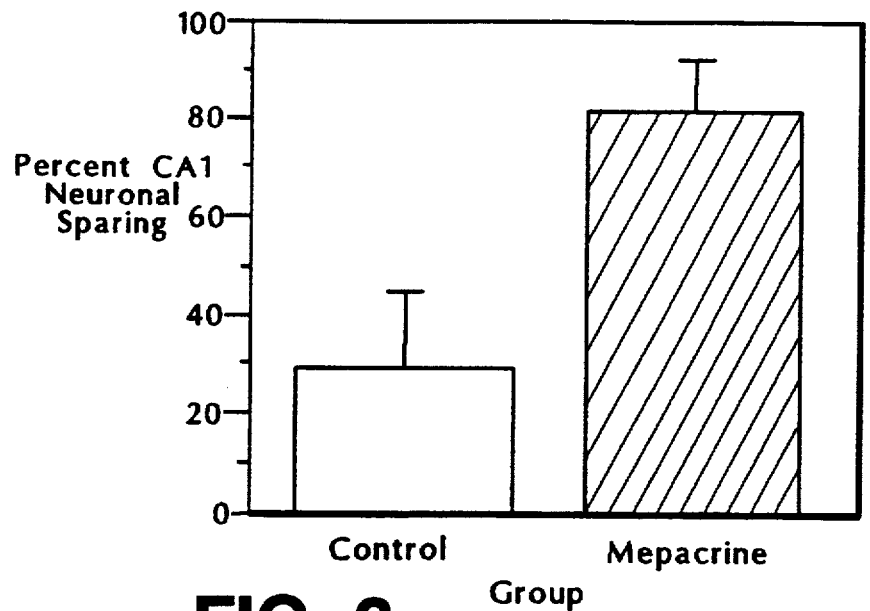
FIG. 8 is a graph of the effect of one hour post-treatment with mepacrine on ischemia-induced hippocampal damage.

As shown in FIG. 8, gerbils treated with mepacrine one hour after ischemic injury had approximately 80±10% sparing of CA1 pyramidal cells, while only 27±15% sparing of CA1 pyramidal cells was observed in untreated gerbils. Gerbils received mepacrine (80 mg/kg, ip) (crossed hatched bar), or vehicle (control) (solid bar), one hour following, and once a day (40 mg/kg, ip) for 4 days after bilateral occlusion of the carotid arteries. The gerbils were killed on the fourth postoperative day, and damage to the CA1 region of the hippocampus was evaluated as described below. The mean size of the intact pyramidal cell layer is expressed above as a percentage of the total CA1 pyramidal cell subfield for each group, ±S.E.M. (0%=total neuronal loss; 100%=maximum possible sparing).

Transient forebrain ischemia was induced under Nembutal anesthesia (50 mg/kg intraperitoneally) in male Mongolian gerbils weighing 50-80 g. An anterior ventral midline incision was made, the right and left common carotid arteries were isolated from the vagus nerve, and suture thread was tied around each artery to achieve total occlusion of blood flow for a period of 5 minutes. At the end of the ischemic period, the suture threads were removed, and the incision was closed with wound clips after ascertaining that blood flow was completely restored to both carotid arteries. The gerbils received mepacrine (80 mg/kg, intraperitoneally) immediately prior to or one hour following ischemia, and once a day (40 mg/kg, intraperitoneally) for 6 or 4 days after the surgery. The gerbils were killed by decapitation and the brains were rapidly removed and frozen on dry ice. A series of slide-mounted coronal sections from each brain was stained with thionin and examined microscopically. The area of pyramidal cell damage in the CA1 subfield of both hippocampi was measured using a Bioquant image analysis system (R and M Biometrics, Nashville, Tenn.). The area of intact CA1 pyramidal cells was expressed as a percentage of the area of the total CA1 pyramidal cell subfield. Five minute bilateral occlusion of the carotid arteries results in a significant induction of spectrin breakdown, and virtually total bilateral destruction of the CA1 pyramidal cell layer in this animal model of stroke.

Treatment with Mepacrine Completely Prevents Degeneration of Septal Neurons After Traumatic Transection of the Fimbria-Fornix Transection of the fimbria-fornix results in retrograde degeneration of cholinergic neurons in the ventral forebrain. In the human brain, degeneration of these cells is one of the characteristics of Alzheimer's disease and may underlie the memory impairment that is suffered by Alzheimer's victims; as a result, transection of the fimbria-fornix in animals has been used as a model of Alzheimer's disease (Hefti and Weiner, 1986, *Ann. Neurol.* 20:275). Previous studies have shown that central administration of nerve growth factor (NGF) prevents, or "rescues" septal cholinergic neurons from degeneration following transection of the fimbria fornix (Williams et al., 1986, *Proc. Natl. Acad. Sci. USA*, 83:9231; Hefti, 1986, *J. Neurosci.*, 6:2155). The survival of septal neurons in this model has previously been confirmed and quantitated by immunocytochemical detection of the NGF receptor, or messenger RNA for the NGF receptor (NGFr mRNA) using in situ hybridization histochemistry (Springer et al., 1987, *J. Neurosci. Res.*, 17:111, hereby incorporated by reference; Springer et al., 1989, *Soc. Neurosci. Abstr.*, 15:707, hereby incorporated by reference). It was recently found that surgical transection of the fimbria-fornix results in a significant induction of spectrin breakdown in the septum, suggesting a role for CAPA in the retrograde degeneration of septal cholinergic neurons (Roberts-Lewis et al., 1990, *Soc. Neurosci. Abstr.* 16:983).

Figure 9:
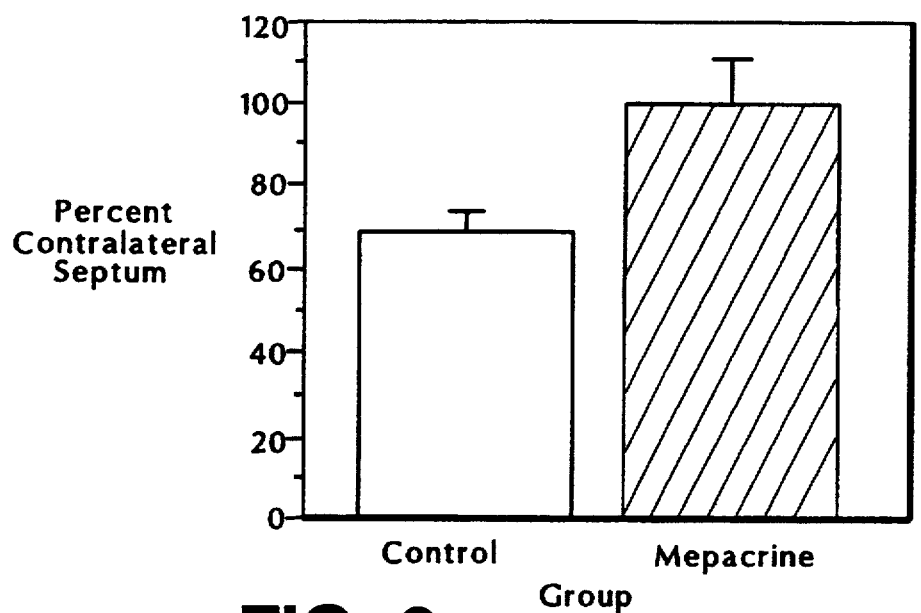
FIG. 9 is a graph of the effect of mepacrine treatment on septal NGFr mRNA after fimbria fornix transection.

As shown in FIG. 9 systemic mepacrine treatment was found to completely prevent the retrograde degeneration of NGFr-bearing septal neurons following surgical transection of the fimbria-fornix in rats.

Female Sprague-Dawley rats (200-250 g) were anesthetized with Nembutal (50 mg/kg, intraperitoneally), and a knife (4 mm wide and 2 mm long) was inserted into the brain at a position approximately −1.0 mm posterior from the bregma, 1 mm lateral from the midline, and 4.5 mm ventral from the top of the skull. The knife was moved several times from side to side and up and down in order to completely transect the fibers of the fimbria. At the time of fimbria-fornix transection, the rats received either a placebo (solid bar in FIG. 9) or 400 mg of mepacrine (cross hatched bar in FIG. 9) subcutaneously, in slow release tablets delivering approximately 20 mg/day (200 mg tablets, Innovative Research of America). The rats were killed 4 days later, and a series of coronal sections from each brain was hybridized with a cRNA probe against nerve growth factor receptor (NGFr) mRNA using in situ hybridization histochemistry with a modification (Baldino et al., 1989, *Soc. Neurosc., Abstr.*, 15:864, hereby incorporated by reference) of the method described by Springer et al. (Springer et al., 1990, *Cell. Mol. Neurobiol.*, 10:33–39, hereby incorporated by reference). The slides were examined microscopically, and positively labelled neurons in the septum ipsilateral to the knife cut were counted and expressed as a percentage of the number of NGFr mRNA-positive neurons in the contralateral (control) septum.

Use

The invention provides a method for the safe, effective treatment of neurological disorders through the use of mepacrine, chloroquine, or hydroxychloroquine. The neurological disorders that may be treated include those neurological disorders thought to involve calcium-sensitive neuronal degradation, including Alzheimer's disease, Parkinson's disease, Huntington's disease, AIDS dementia, stroke and related ischemic/anoxic disorders, epilepsy, motor neuron diseases, peripheral nerve degeneration, and head and spinal cord injuries.

In the practice of the present invention, mepacrine, chloroquine or hydroxychloroquine may be administered orally or parenterally. The mode of administration, dosage, and formulation of these compounds depends upon which neurological disorder is being treated and the general health and level of consciousness of the patient. Appropriate methods of administering these compounds, including dosage and formulation, will be apparent to those skilled in the art, particularly with reference to earlier pharmacological information (e.g., Martindale, The Extra Pharmacopoeia, supra).

Other Embodiments

Other embodiments are within the following claims, e.g., any of mepacrine, chloroquine or hydroxychloroquine may also be provided in combination with other compounds which would be expected to reduce the cellular supply of calcium that activates CAPA, particularly (1) calcium channel blockers (e.g., flunarizine, verapamil, nimodipine, nifedipine); or (2) antagonists of the receptor-mediated entry of calcium, such as antagonists of EAA receptors, or other receptors known to mediate calcium influx (e.g., receptors for angiotensin II or bradykinin). Again, appropriate methods of administering combinations of these compounds, including dosage and formulation, will be apparent to those skilled in the art.

The treatment of the invention can also be used to inhibit cell death from ischemia in non-neural tissues, e.g., in muscle tissue, e.g., smooth muscle, e.g., cardiac muscle.

Chloroquine, mepacrine, and hydroxychloroquine each have an asymmetric carbon at the e position in the N sidechain. The isomers of a racemic mixture of any of these compounds can be separated by methods known to those skilled in the art and the isomeric preparations thus purified tested, by methods known to those skilled in the art, to determine if an isomeric preparation (as opposed to a racemic mixture) is more desirable, e.g., has less toxicity or greater potency, for use in the methods of the invention.

It is understood that various other modifications will be apparent and can readily be made by those skilled in the art without departing from the scope and spirit of the invention. In particular, it will be straightforward to evaluate the neuro-protective activity of derivatives of mepacrine, chloroquine, or hydroxychloroquine by the methods described herein.

What is claimed is:

1. A method for inhibiting necrosis resulting from a cerebral ischemia in a mammal in need thereof, comprising administering to said mammal an amount of a preparation effective to inhibit said necrosis, said preparation comprising any of mepacrine, chloroquine, or hydroxychloroquine, said preparation being essentially free of colchicine.

2. The method of claim 1, wherein said necrosis is the result of a calcium related disorder.

3. The method of claim 1, wherein said necrosis is the result of a disease of a cerebral motor neuron or an injury to the head or spinal cord.

4. The method of claim 1, wherein said necrosis occurs in the hippocampus.

5. The method of claim 1, wherein said necrosis occurs at a cholinergic neuron.

6. The method of claim 1, wherein said necrosis occurs in the substantia nigra.

7. The method of claim 1, wherein said necrosis occurs at a dopaminergic neuron.

8. The method of claim 1, wherein said necrosis occurs in the basal ganglia.

9. The method of claim 1, wherein said necrosis occurs at a neuron that comprises a nerve growth factor receptor.

10. The method of claim 1, wherein said necrosis occurs in the spinal cord.

11. The method of claim 1, wherein said necrosis occurs at a cerebral motor neuron.

12. The method of claim 1, wherein said necrosis occurs at a GABAergic neuron.

13. The method of claim 1, wherein said necrosis occurs in the subcortex.

14. The method of claim 1, wherein said necrosis occurs in the ventral forebrain.

15. The method of claim 1, wherein said necrosis occurs in the cortex.

16. The method of claim 1, wherein said necrosis results in stroke.

* * * * *